(12) United States Patent
Mason

(10) Patent No.: US 7,807,101 B2
(45) Date of Patent: Oct. 5, 2010

(54) METHODS OF USING CHLORINE DIOXIDE AS A FUMIGANT

(75) Inventor: John Y. Mason, Slingerlands, NY (US)

(73) Assignee: Sabre Intellectual Property Holdings Company LLC, Slingerlands, NY (US)

(*) Notice: Subject to any disclaimer, the term of this patent is extended or adjusted under 35 U.S.C. 154(b) by 0 days.

(21) Appl. No.: 11/270,973

(22) Filed: Nov. 11, 2005

(65) Prior Publication Data
US 2006/0228253 A1 Oct. 12, 2006

Related U.S. Application Data

(63) Continuation-in-part of application No. 09/997,694, filed on Nov. 30, 2001, now abandoned.

(51) Int. Cl.
*A61L 2/20* (2006.01)
(52) U.S. Cl. ............................ 422/28; 422/37; 422/123
(58) Field of Classification Search ................ 422/1, 422/4, 28, 29, 37, 123, 305
See application file for complete search history.

(56) References Cited

U.S. PATENT DOCUMENTS

| | | | | |
|---|---|---|---|---|
| 4,681,739 A | * | 7/1987 | Rosenblatt et al. | 422/37 |
| 4,780,333 A | * | 10/1988 | Smith et al. | 427/236 |
| 5,006,326 A | * | 4/1991 | Mayurnik et al. | 423/477 |
| 5,961,936 A | | 10/1999 | Heredia | |
| 2004/0022667 A1 | * | 2/2004 | Lee et al. | 422/4 |

FOREIGN PATENT DOCUMENTS

JP 401034904 A * 2/1989

OTHER PUBLICATIONS

U.S. Environmental Protection Agency, Office of Pesticide Programs. Notice of Pesticide: Registration. Name of Pesticide Product: CD-Cartridge. Registrant: Advanced Sterilization Products. Date of Issuance: Sep. 2, 1999.

"Pharmacy Alumni News", University of Pittsburgh School of Pharmacy, Pittsburgh, PA. Summer 2001.

"Sterilization Equipment Evaluation Report", TUV Product Service, Santa Clara, CA, Feb. 7, 2001.

"Cloridox-GMP Sterilization System, System Operations Guide", ClorDiSys Solutions, Inc., Lebanon, NJ, 2002.

Eylath, A., Wilson, D.L., Thatcher, D., and Pankau, A., "Successful Sterilization Using Chlorine Dioxide Gas", BioProcess International, Jul. 2003.

Leo, F., Poisson, P., Sinclair, C.S., Tallentire, A., "Design, Development and Qualification of a Microbiological Challenge Facility to Assess the Effectiveness of BFS Aseptic Processing", J. of Pharmaceutical Science and Technology, vol. 59, No. 1, Jan.-Feb. 2005.

(Continued)

*Primary Examiner*—Sean E Conley
(74) *Attorney, Agent, or Firm*—Heslin Rothenberg Farley & Mesiti PC; Alana M. Fuierer

(57) ABSTRACT

The invention provides methods of using chlorine dioxide gas for the fumigation of building spaces, heating ventilation and air conditioning systems (HVAC, e.g., return supply ducts, heating and cooling coils and the like), vehicles, office spaces, process equipment, files, documents, mail, mail processing equipment, industrial process equipment and consumer related items under safe conditions.

17 Claims, 1 Drawing Sheet

OTHER PUBLICATIONS

Eylath, A., "Successful High-Level Disinfection of Process Vessels Using Chlorine Dioxide Gas", Philadelphia, PA., Annual Meeting 2000.

Eylath, A., "Successful High-Level Disinfection of an Aseptic Fill Isolator Using Chlorine Dioxide Gas", Isolation Technology Conference, Irvine, CA., Oct. 16, 2000.

Battisti, Diane L., Ph.D., "Gaseous Chlorine Dioxide-Application of the Sterilant for Decontamination of a 6000-ft Room Implications for Laboratory/Animal Facilities", May 2001.

Westphal, A., Buford Price, P., Leighton, T., Wheeler, K., "Kinetics of size changes of individual Bacillus thuringiensis spores in response to changes in relative humidity", PNAS, vol. 100, No. 6, pp. 3461-3466, Mar. 18, 2003.
Sloan, R. and Plocic, M., "Chlorine Dioxide Disinfectant Feasibility Study", Technical Report, Baylor College of Medicine, Houston Medical Center, Houston, TX, Jul. 9, 2001.
Waddell, D. and Metch, J., "Chlorine Dioxide Disinfectant Feasibility Study", Technical Report, Baylor College of Medicine, Houston Medical Center, Houston, TX, Mar. 13, 2001.
Czarneski, M. and Lorcheim, P., "Isolator Decontamination Using Chlorine Dioxide Gas," Pharmaceutical Technology, pp. 124-133, Apr. 2005.
"ISODOX Sterilization System, System Reference Guide", Advanced Sterilization Products, Irvine, CA.
Memo to Archie Woodworth from Paul Lorcheim, re: Chlorine Dioxide Gas Generator Quotation and Various Invoices (various dates).
Environmental Assessment, Applicant: Bio-Cide International, Inc., Jan. 14, 2007.
Jeng, D. and Woodworth, A., "Chlorine Dioxide Gas Sterilization under Square-Wave Conditions", Applied and Environmental Microbiology, pp. 514-519, Feb. 1990.
Eylath, A., Madhogarhia, S., Rivera, E., Lorcheim, P. and Czarneski, M., "Successful Sterilization Using Chlorine Dioxide Gas, Part Two: Cleaning Process Vessels", J. of BioProcess International, Aug. 2003.
Battisti, D., "Development of a Chlorine Dioxide Sterilization System", Dissertation, University of Pittsburgh, 2000.
Kowalski, J.B., Hollis, R.A. and Roman, C.A., "Sterilization of overwrapped foil suture packages with gaseous chlorine dioxide", J. of Industrial Microbiology, pp. 239-245, 1988.
Battisti, D., "Use of the ISODOX Sterilization System for Decontamination of Barrier Isolators and Sealed Enclosures", Barnett International, Jan. 29-30, 2001.
Advertisement entitled "Features of the Chlorine Dioxide Gas Generation System" (undated).

* cited by examiner

METHODS OF USING CHLORINE DIOXIDE AS A FUMIGANT

CROSS-REFERENCE TO RELATED APPLICATIONS

This application claims the benefit of and is a continuation-in-part of U.S. patent application Ser. No. 09/997,694, filed Nov. 30, 2001, now abandoned, the disclosure of which is incorporated herein by reference in its entirety.

BACKGROUND OF THE INVENTION

Gas fumigation as currently practiced uses either ethylene oxide (epoxyethane, ETO), formaldehyde, vaporized peroxide or ozone. Each of these fumigants has disadvantages that limit their utility in fumigating large volumes, e.g. buildings or vehicles. Ethylene oxide is a flammable and explosive gas that is classified as both a mutagen and a carcinogen. The use of ethylene oxide as a fumigant requires extensive post detoxification and clean up procedures. Formaldehyde is potentially explosive and an occupational carcinogen. Moreover, it has poor penetrating ability. The use of formaldehyde as a fumigant requires extensive post detoxification and clean up procedures. Vaporized peroxide reacts generally with all organic compounds in the environment to be fumigated, thus having a high demand for fumigant. Vaporized peroxide is effective in fumigating spaces of volume less than 1200 $ft^3$. Ozone reacts generally with all organic compounds in the environment to be fumigated, and has the shortest half-life of these fumigants, making ozone even less suitable than vaporized peroxide for the fumigation of large volumes.

Chlorine dioxide is recognized as an effective sterilant. However, no guidance is available regarding the use of chlorine dioxide for the fumigation of large volumes. Sodium hypochlorite is known to be useful and effective for scrubbing down surfaces. However, such procedures using sodium hypochlorite are labor intensive, affect appearance and integrity of materials scrubbed, and are not as suitable for large scale use as are the gas methods. Chlorine gas is also not suitable due to the health hazards, high corrosivity of the gas, and the production of chlorinated organic by-products.

Chlorine dioxide, which is a selective oxidant and a protein synthesis deactivator, has been reported to be efficacious against *Bacillus subtilis* (a gram positive, chemoorganotroph spore former similar to *Bacillus anthracis*) under controlled laboratory medical sterilizer conditions.

SUMMARY OF THE INVENTION

The present invention provides methods for the effective large-scale use of chlorine dioxide to allow for gaseous penetration of contents included within in a large enclosed volume requiring fumigation and sterilization in an environmentally safe manner. The present invention provides a method comprising the steps of:

climatizing a volume requiring fumigation containing contents;

generating chlorine dioxide gas;

introducing the chlorine dioxide gas into the volume requiring fumigation;

distributing the introduced chlorine dioxide gas in the volume requiring fumigation;

maintaining a residual amount of the chlorine dioxide gas within the volume requiring fumigation under environmentally safe conditions at a level and duration permitting gaseous penetration of included contents as required for decontamination; and removing the chlorine dioxide gas from the volume requiring fumigation, thereby fumigating the large enclosed volume and contents and restoring habitability.

In one preferred embodiment, the chlorine dioxide gas is removed from the volume requiring fumigation with the same equipment that was used to introduce the chlorine dioxide gas.

In one embodiment, the present invention provides a process comprising producing chlorine dioxide by using an apparatus such as a chlorine dioxide generator. In one embodiment, the chlorine dioxide is generated directly as a gas. In another embodiment, the chlorine dioxide is generated as a solution of chlorine dioxide gas in a liquid. In one preferred embodiment, the liquid is water. In an aqueous solution, chlorine dioxide solution equilibrium partial pressure is optimally kept below about 26,000 ppm V.

The generated chlorine dioxide is transferred directly, or alternatively, indirectly via a storage tank, to a high gas:liquid ratio emitter. In one preferred embodiment, the emitter is an apparatus such as a gas/liquid contactor having a high efficiency mist eliminator and very low liquid/gas rates. In one embodiment, the emitter is an apparatus such as a stripper.

The emitter is operated to maintain the gaseous chlorine dioxide concentration substantially below the explosion limit of chlorine dioxide in the air. Prior to generation of the chlorine dioxide, the emitters are used with water alone to raise the relative humidity in the volume requiring fumigation, with adjustment of the temperature. Alternatively, the humidification and fumigation can be done simultaneously using the same apparatus by the appropriate adjustment in the temperature of chlorine dioxide solution.

The treatment is conducted in reduced illumination, preferably substantially dark, to minimize the decomposition of chlorine dioxide to chlorine. The process is monitored with the use of an infrared camera or similar device.

If the space to be fumigated contains materials that are potentially susceptible to corrosion, the chlorine dioxide should be of the highest possible purity. Specifically, chlorine gas should be present in the introduced gas at a level less than about 5%, preferably less than about 0.5%. Suitably chlorine dioxide gas is present at a concentration in the introduced gas of at least 90%, preferably at least 95%, and optimally at least 99%.

Once the desired relative humidity and temperature are attained, then the variable generation rate of chlorine dioxide gas is initiated. The initial rate is high to provide sufficient chlorine dioxide to penetrate the various surfaces demands within the volume requiring fumigation. This rate is predetermined to accommodate the surface demand as well as to provide the initial charge of the volume requiring fumigation to a predetermined chlorine dioxide residual level. The chlorine dioxide generation rate is then reduced appropriately to maintain the predetermined chlorine dioxide concentration in the air of the volume requiring fumigation for a predetermined time. This can be achieved by a number of means, such as lowering the concentration of chlorine dioxide in the solution that is fed to the emitter, or lowering the flow rate of the chlorine dioxide solution to the emitter.

The maintenance level of chlorine dioxide gas concentration is determined to compensate for the decay or loss rate from the volume requiring fumigation. The volume requiring fumigation is preferably to be at slightly negative pressure to areas outside of it and efforts are made to seal off the volume through the use of strippable sealant, such as foam that sets up hard. Once the required time weighted average concentration and contact time are attained, then the generation of chlorine dioxide is stopped.

The generator, storage and emitter are then purged with fresh water. Once this is complete, the water is injected with an alkalizing and dechlorinating agent or other functional chemistry (e.g., ascorbic acid), that will absorb the chlorine dioxide. This scrubbing solution is then fed to the emitter and with the blowers still in operation, the emitter begins to scrub chlorine dioxide out of the environmental air composition within the said volume that has been fumigated. This process is continued until the environmental air composition within the volume that has been fumigated is returned to acceptable limits for reopening to the exterior environment and rehabitation.

The emitters can be located inside or outside of the volume requiring fumigation. However, it is highly preferred to locate the emitter inside the volume requiring fumigation, since then no contaminated air is allowed to leave the volume requiring fumigation.

DESCRIPTION OF A PREFERRED EMBODIMENT

Figure 1:
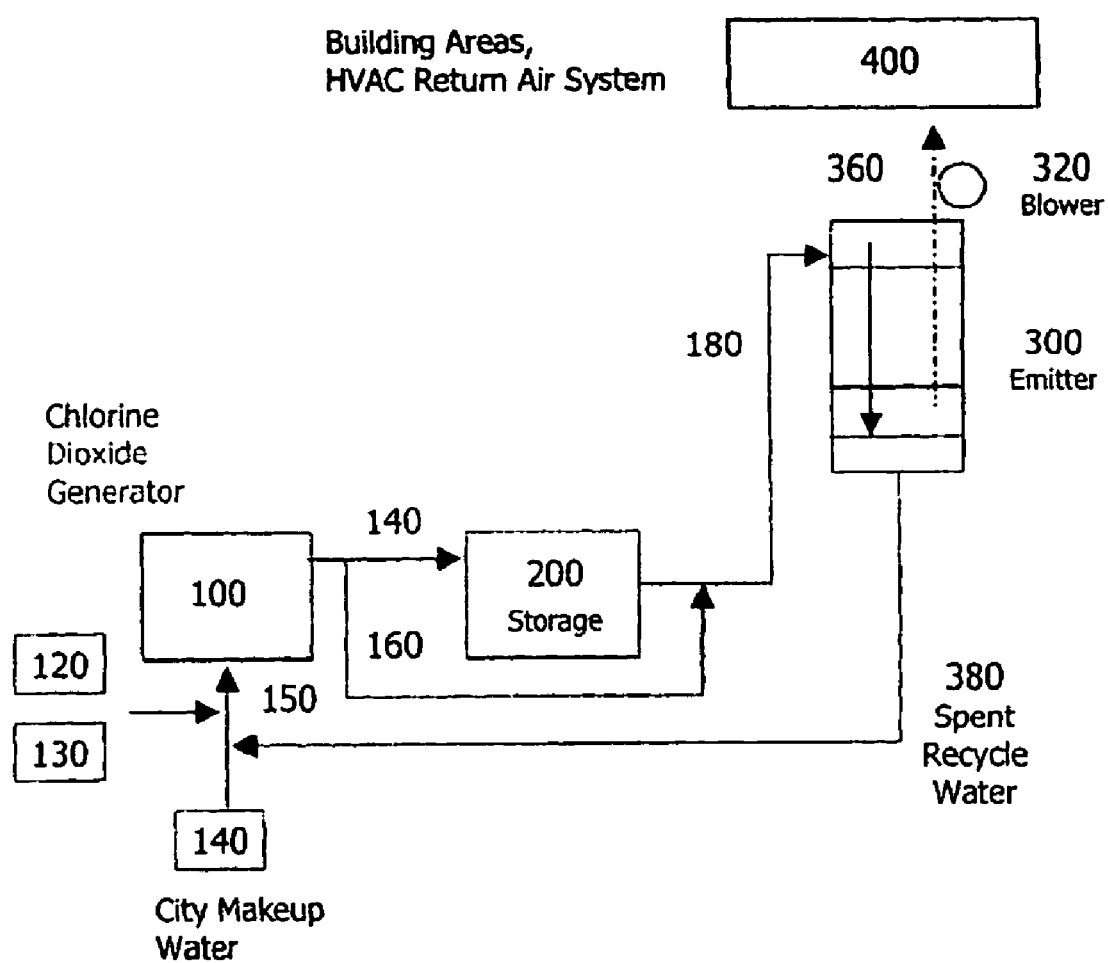
FIG. 1 is a schematic illustration of one embodiment of the present invention.

The present invention can be further understood by reference to FIG. 1, which schematically illustrates one embodiment of the invention. The invention is practiced using a chlorine dioxide gas generator 100 that provides chlorine dioxide dissolved in water 180 directly 160, or alternatively, indirectly 140 via storage 200, to a emitter 300 comprising a blower 320 that produces chlorine dioxide gas in air 360 for treatment of building areas and/or a heating, ventilation and air conditioning (HVAC) return air system of a building 400.

The chlorine dioxide generator 100 receives an input 150 that is a mixture of city makeup water 140 and chemicals 120 or 130. Suitable mixing means are used to combine the city makeup water 140 and chemicals 120 or 130. Metering means are used to regulate the amounts and proportions of the city makeup water 140 and chemicals 120 or 130 that are combined. In the initial climatizing stage of the process, water alone is provided to the input 150 of the chlorine dioxide generator 100, in order to adjust the relative humidity of the volume to be treated. In the second stage of the process, chlorine dioxide precursor chemicals 120 are combined with the city makeup water 140. Several chemical means of generating chlorine dioxide, and their corresponding chlorine dioxide precursor chemicals are known in the art, and the choice of suitable means and chemicals is within the abilities of the skilled artisan. Exemplary chemical means of generating chlorine dioxide are disclosed in U.S. Pat. Nos. 4,689,169 (Mason et al.), 5,204,081 (Mason et al.), 5,227,306 (Eltomi et al.), 5,258,171 (Eltomi et al.) and 5,965,004 (Cowley et al.), the teachings of which are hereby incorporated by reference.

The output of the chlorine dioxide generator 100 can be routed directly 160 to provide chlorine dioxide dissolved in water 180 to the emitter 300. Alternatively, the output of the chlorine dioxide generator can be routed 140 to a storage means 200, from which chlorine dioxide dissolved in water 180 can be routed to the emitter 300.

The emitter 300 removes chlorine dioxide from the water and delivers chlorine dioxide in air 360 by duct means to the volume to be fumigated, in general, building areas and/or a HVAC return air system. "Duct means" includes, but is not limited to, temporary or permanent ductwork, pipes, hoses and the like. Water 380 recovered from the emitter can be recycled and combined by mixing means with city makeup water 140 and chemicals 120 or 130 to provide input 150 to the chlorine dioxide generator 100.

In a third stage of the process, the chlorine dioxide generator 100, storage 200 and emitter 300 are flushed with water alone. During a further stage of the process, detoxification chemicals 130 are combined with water to provide the input to the chlorine dioxide generator 100.

Monitoring and controlling the dew point within the volume requiring fumigation is a significant aspect. During the process of fumigation, steps must be taken to avoid condensation. Therefore during the entire fumigation process the atmosphere within the volume requiring fumigation must be carefully controlled using space heaters or the HVAC system both to avoid over-humidification and to regulate the temperature of the chlorine dioxide solution fed to the emitter. Failure to control these factors can lead to spot damage as well as a higher use to chlorine dioxide.

Example 1

The environment within the enclosed volume of a trailer is fumigated and restored to habitability as follows. Initially, the environment is climatized to a temperature of 70-80° F. and a relative humidity of 60-80%. During treatment, chlorine dioxide is introduced into the volume to be fumigated and maintained at a residual level of 500 ppm V for 10 hours. In other embodiments, the residual chlorine dioxide level is maintained at about 750 ppm V, about 1000 ppm V or about 3000 ppm V and the treatment time is in the range of about 8 to about 12 hours. Typically, if the enclosed volume is 2280 $ft^3$, air is suitably recirculated at 5 CFM. The treatment is conducted in reduced illumination, preferably substantially dark, to minimize the decomposition of chlorine dioxide to chlorine. Suitably chlorine dioxide gas is present at a concentration in the introduced gas of at least 90%, preferably at least 95%, and optimally at least 99%.

If the space to be fumigated contains materials that are potentially susceptible to corrosion, the chlorine dioxide should be of the highest possible purity. Specifically, chlorine gas should be present in the introduced gas at a level less than about 5%, preferably less than about 0.5% Efficacy is measured by percent inactivation of *Bacillus subtilis* spores used as monitors. The contents of the trailer are inspected to determine the discoloration and functionality of all the material placed in trailer, including drapes, chairs, files, mail and other documents and computers. Apart from a slight discoloration, no discernible effects on carpets, drapes, furniture and office equipment (e.g., copiers, computers, printers, etc.) are found. No chlorine is found in the treated space after fumigation.

Example 2

The environment within an enclosed volume was fumigated and restored to habitability as follows. HVAC equipment is inspected and fans readied. All filters are removed and burned. Cooling and heating coils are sprayed with degreaser/detergent. The environment is climatized for 2.5 hours to a temperature of 60-80° F., suitably about 75° F., and a relative humidity of 70-80%, suitably about 75%. The pH of the city water is adjusted to 6.5-7.0 to allow the emitters to deliver free $ClO_2$ into the air. The building is sealed with strippable foam and air loss rate measure and used to correct the calculated chlorine dioxide dosage needed for fumigation.

Additional internal fans are placed in positions determined by modeling to assist the HVAC in approaching ideal mixing. Chlorine dioxide is introduced with an air flow rate of 2,000 CFM and maintained at a level of 500 ppm for about 12 hours. The initial charge of the enclosed volume with chlorine dioxide is rapid to prevent any pathogens from reacting to the hostile environment. Typically the chlorine dioxide in the enclosed air rises to 7-14 ppm a few minutes and is greater than 30 ppm within five minutes. Efficacy of fumigation is measured by percent inactivation of *Bacillus subtilis* spores that are used as monitors.

The equipment is converted to scrubbers by rinsing chlorine dioxide and emitter with water alone followed by a mixture of bisulfite and caustic in water that absorbs $ClO_2$ and $Cl_2$ The environmental air is detoxified for 28-32 hours or the exchange of about 30-32 building volumes, in order to reduce chlorine dioxide levels in the building air to less than about 0.1 $mg/m^3$. It has been found that the chlorine dioxide levels typically decay at a rate of about 100 ppmV per hour, depending on the contents included within the volume requiring fumigation. The volume requiring fumigation can be detoxified very quickly, typically in about 5-6 hours.

The building air is recirculated with the air conditioning on to lower the relative humidity to less than about 35%. The HVAC heating and cooling coils are sprayed with chlorine dioxide and the HVAC filters are replaced with new filters.

The present invention is not to be limited in scope by the specific embodiments described herein, but by the appended claims. The described embodiments are intended as illustrations of individual aspects of the invention, and functionally equivalent methods and components are within the scope of the invention. Indeed, various modifications of the invention, in addition to those shown and described herein will become apparent to those skilled in the art from the foregoing description and accompanying drawing. Such modifications are intended to fall within the scope of the appended claims.

The invention claimed is:

1. A method suitable for fumigating an enclosed volume and contents requiring fumigation and restoring habitability, comprising the steps of:

a) climatizing the enclosed volume and contents therein;

b) combining water and chlorine dioxide, thereby generating an aqueous solution of chlorine dioxide;

c) removing chlorine dioxide from the aqueous solution and introducing chlorine dioxide gas in a gaseous phase into the enclosed volume via an emitter;

d) distributing the chlorine dioxide gas throughout the enclosed volume;

e) maintaining a residual amount of the chlorine dioxide gas within the enclosed volume under environmentally safe conditions and at a level and duration to enable gaseous penetration of the contents as required for decontamination, thereby fumigating the enclosed volume and contents therein;

f) introducing detoxification scrubbing chemicals into the aqueous solution to remove chlorine dioxide from the aqueous solution and stop flow of chlorine dioxide gas from the emitter into the enclosed volume, thereby allowing the chlorine dioxide gas within the enclosed volume to decrease to acceptable levels and restore habitability; and g) recirculating water recovered from the aqueous solution of step c) to supply a continuous source of water for step b) and/or step f) in a closed-loop, continuous process.

2. The method of claim 1 wherein the emitter comprises a gas stripper.

3. The method of claim 1 wherein the step of climatizing the enclosed volume comprises adjusting the relative humidity in the enclosed volume.

4. The method of claim 1 wherein the step of climatizing the enclosed volume comprises adjusting the temperature.

5. The method of claim 1 wherein the step of climatizing the enclosed volume comprises avoiding exceeding the dew point.

6. The method of claim 1 wherein the step of climatizing the enclosed volume comprises reducing the level of illumination.

7. The method of claim 1 wherein the enclosed volume requiring fumigation is a building or portion thereof.

8. The method of claim 1 wherein the enclosed volume requiring fumigation is a vehicle or portion thereof.

9. The method of claim 1 wherein the distributing step comprises using a heating ventilation and air conditioning (HVAC) system.

10. The method of claim 1 wherein the enclosed volume requiring fumigation is maintained substantially dark.

11. The method of claim 1 wherein the concentration of chlorine dioxide gas present in the gaseous phase of step c) is at least 90%.

12. The method of claim 1 wherein the concentration of chlorine dioxide gas present in the gaseous phase of step c) is at least 95%.

13. The method of claim 1 wherein the concentration of chlorine dioxide gas present in the gaseous phase of step c) is at least 99%.

14. The method of claim 1 wherein the emitter used in step (c) is also used to climatize the enclosed volume requiring fumigation.

15. The method of claim 1 wherein the step of climatizing comprises maintaining the enclosed volume at a temperature that ranges from about 60° F. to about 80° F. and a relative humidity that ranges from about 60% to about 80%.

16. The method of claim 1 wherein the emitter is located inside the volume requiring fumigation.

17. The method of claim 1 wherein the emitter is located outside the volume requiring fumigation.

* * * * *